United States Patent
Pennemann et al.

(10) Patent No.: US 11,702,381 B1
(45) Date of Patent: Jul. 18, 2023

(54) METHOD FOR OPERATING A RECTIFICATION COLUMN

(71) Applicants: Covestro Deutschland AG, Leverkusen (DE); Covestro LLC, Pittsburgh, PA (US)

(72) Inventors: Bernd Pennemann, Bergisch Gladbach (DE); Shuang Liang, Houston, TX (US); Zhangyong Ming, Shanghai (CN); Juergen Bausa, Kürten (DE)

(73) Assignees: Covestro Deutschland AG, Leverkusen (DE); Covestro LLC, Pittsburgh, PA (US)

( * ) Notice: Subject to any disclaimer, the term of this patent is extended or adjusted under 35 U.S.C. 154(b) by 0 days.

(21) Appl. No.: 17/678,360

(22) Filed: Feb. 23, 2022

(51) Int. Cl.
  *B01D 3/42* (2006.01)
  *C07C 209/86* (2006.01)
  *B01D 3/32* (2006.01)

(52) U.S. Cl.
  CPC ............ *C07C 209/86* (2013.01); *B01D 3/322* (2013.01); *B01D 3/4205* (2013.01); *B01D 3/4211* (2013.01)

(58) Field of Classification Search
  CPC ............ B01D 3/42–4294; B01D 3/4216–4255
  See application file for complete search history.

(56) References Cited

U.S. PATENT DOCUMENTS 3,238,111 A * 3/1966 Harper .................. B01D 3/425
  202/160
3,830,698 A 8/1974 Kleiss
  (Continued)

FOREIGN PATENT DOCUMENTS

| EP | 0460037 A1 | 12/1991 |
| EP | 1746083 A1 | 1/2007 |
| WO | 2021116146 A1 | 6/2021 |

OTHER PUBLICATIONS

Luyben, Practical Distillation Control, 1992, Van Nostrand Reinhold, p. 158.

(Continued)

*Primary Examiner* — Jonathan Luke Pilcher
(74) *Attorney, Agent, or Firm* — Donald R. Palladino

(57) ABSTRACT

The present invention provides a method for operating a rectification column (1000) for separating a mixture (S) containing a component A and a component B having a boiling point higher than that of the component A at an operating pressure of the rectification column (1000) which is lower than ambient pressure, wherein the method comprises a step for controlling the mass fraction of the component B in the product stream of the component A (P1) to a value within a first target range from 0.1% to 5.0% and the mass fraction of the component A in the product stream of the component B (P2) to a value within a second target range from 0.1% to 5.0%, wherein the control is carried out as a function of a controlling temperature (TC) for which a setpoint $TC_{setpoint}$ is calculated according to the equation $TC_{setpoint}=T2+F\cdot(T1-T2)$, where F is a factor which is in the range from 0.1 to 0.9 and T1 and T2 are reference temperatures, wherein in the case of a deviation in the measured control temperature (TC) from its setpoint $TC_{setpoint}$ being found the control temperature (TC) is readjusted to the setpoint $TC_{setpoint}$ by varying one or more of the following actuating variables: (i) heating of the column bottom (130) by the evaporator (200), (ii) the mass flow $\dot{m}_{A42}$ of the reflux (A42) fed back into the rectification column, (iii) the mass flow $\dot{m}_{P2}$ of the product stream P2 and (iv) the mass flow $\dot{m}_{P1}$ of the product stream P1.

15 Claims, 3 Drawing Sheets

(56) References Cited

U.S. PATENT DOCUMENTS

| | | | |
|---|---|---|---|
| 4,024,027 | A | 5/1977 | Boyd |
| 5,368,699 | A | 11/1994 | Rhiel et al. |
| 6,359,177 | B1 | 3/2002 | Brady et al. |
| 2019/0184304 | A1* | 6/2019 | Schweigert ............ B01D 3/425 |

OTHER PUBLICATIONS

Kister, Distillation Operation, 1990, McGraw-Hill Education, pp. 555 to 557 and pp. 563 to 566.
European Search Opinion dated Aug. 18, 2022, EP Application No. 22 161 178.3.

* cited by examiner

METHOD FOR OPERATING A RECTIFICATION COLUMN

FIELD

The present invention provides a method for operating a rectification column (1000) for separating a mixture (S) containing a component A and a component B having a boiling point higher than that of the component A at an operating pressure of the rectification column (1000) which is lower than ambient pressure, wherein the method comprises a step of controlling the mass fraction of the component B in the product stream of the component A (P1) to a value within a first target range from 0.1% to 5.0% and the mass fraction of the component A in the product stream of the component B (P2) to a value within a second target range from 0.1% to 5.0%, wherein the control is carried out as a function of a control temperature (TC) for which a setpoint $TC_{setpoint}$ is calculated according to the equation $TC_{setpoint}=T2+F \cdot (T1-T2)$, where F is a factor which is in the range from 0.1 to 0.9 and T1 and T2 are reference temperatures, wherein in the case of a deviation in the measured control temperature (TC) from the setpoint $TC_{setpoint}$ being found the control temperature (TC) is readjusted to the setpoint $TC_{setpoint}$ by varying one or more of the following actuating variables: (i) heating of the column bottom (130) by the evaporator (200), (ii) the mass flow $\dot{m}_{A42}$ of the reflux (A42) fed back into the rectification column, (iii) the mass flow $\dot{m}_{P2}$ of the product stream P2 and (iv) the mass flow $\dot{m}_{P1}$ of the product stream P1.

BACKGROUND

In many production processes there are separation tasks in which a mixture of two or more components is to be separated into its constituents. As long as thermal stability, volatility and boiling point differences of the components to be separated permit, such separation tasks are usually achieved by continuous rectification in industrial production. In the simplest case of a mixture S which consists essentially of two components A and B, with B having a higher boiling point than A under the operating conditions selected for the rectification column used, the objective is thus to transfer B into the bottom of the column or into a sidestream taken off in the lower part of the column and transfer A into the top of the column or into a sidestream taken off in the upper part of the column in such a way that the one component is as free of the other component as possible. Depending on structure and operating conditions of the rectification column used, the concentration of A at the outlet point for A and the concentration of B at the outlet point for B changes (concentration profile).

The present invention is concerned with such a separation task—separation of a mixture S consisting essentially (apart from impurities) of two components A and B. Rectification columns which are suitable for such a separation task (and also for more demanding separation tasks) are known in principle from the prior art. The present invention is concerned with a particular concept for controlling such a rectification column, in particular using a temperature control for controlling the position of the concentration profile.

Control of the position of the concentration profile of a rectification column by direct utilization of a column temperature as controlled variable is known per se and is widely used. For this purpose, a position which reacts very sensitively to disturbances is sought in the temperature profile of the column. This position is typically determined with the aid of simulation studies for varied operating conditions. The column temperature at the position determined in this way is then used as control temperature.

However, if fluctuations in the pressure in the column occur at the place where the control temperature is measured, these influence the boiling point and thus the control temperature. This leads to an unwanted reaction of the controller, which ultimately impairs the quality of control. Such pressure fluctuations can be caused firstly by fluctuations in the pressure at the top of the column. However, they can also occur at a constant pressure at the top as a result of the pressure drop in the column being increased or decreased by a change in the column load. If the influence of the pressure is dominant over the influence of the composition, the desired quality of control can only be achieved in a small pressure and load range.

For this reason, a pressure-compensated temperature calculated from the measured column temperature is in many cases used instead of the measured column temperature as control variable. The usual procedure here is to determine the pressure dependence of the boiling point at the position of the temperature sensor by means of simulation calculations of the column, fit a formula, for example the known Antoine equation, to the data, calculate a pressure-compensated temperature therefrom and use this as control variable for controlling the column. A disadvantage of this procedure is that an additional pressure sensor is required. These are also more susceptible to malfunctions and less accurate than temperature sensors. Pressure measurements frequently display an increasing time-dependent deviation (drift) which results, for example, from the loss of hydraulic fluid or from process-related encrustations or deposits.

In the case of packed columns a further problem exists: the control temperature is usually measured in a packed bed. Due to the flowing liquid, pressures are not reliably measurable there. Instead, the pressure measurement will be installed in regions of a pure gas phase, for instance arranged below liquid collectors or above liquid distributors. The pressure at the position of the temperature measurement is then shifted relative to this pressure measurement by the differential pressure over such internals. This differential pressure is also not constant but instead depends on the hydrodynamic properties of the column which are in turn dependent on the throughput. To solve this problem, it is in principle conceivable to provide a pressure measurement above and below the temperature sensor for the control temperature in each case, but this reduces the reliability of the arrangement further. The problems mentioned can become so great that temperature control under certain conditions causes more problems than it solves (cf. Luyben, *Practical Distillation Control*, 1992, Van Nostrand Reinhold, p. 158).

For use of this approach, it is also necessary for deviations which result from measurement errors in the measurement of temperature and pressure to have only a small influence on the calculated pressure-compensated temperature. Particularly in the case of the chemicals having small differences in the boiling point, the achievable accuracy of the pressure measurement is, however, in many cases not sufficient, so that the pressure compensation of the control temperature does not lead to the desired quality of control.

To overcome the above-mentioned problems, control systems which are based on the measurement of temperature differences have been developed. In this case, a reference temperature measurement is inserted at a place in the column at which the boiling point depends on the composition only to a little extent. The temperature difference between this reference temperature measurement and the control temperature measurement is utilized for controlling the column. In this way, pressure changes in the column can be compensated for to a certain extent, but not changes in the differential pressure which once again depends on the column load.

Kister describes in *Distillation Operation*, 1990, McGraw-Hill Education, pp. 555 to 557 and pp. 563 to 566, an approach by Boyd in which two temperature differences, i.e. a total of four temperature sensors, are used to compensate for the influence of the differential pressure. Disadvantages of this procedure are:

a) The temperatures used for forming the differences are inevitably quite close together and the temperature measurements therefore have to be very precise.
b) The calculation of the differential temperatures for the control is very complicated and no longer comprehensible for the plant operator in the case of malfunctions.
c) Four temperature sensors are required.
d) The method is, according to Boyd, only usable when the maximum permissible contents of impurities in the products are in the ppm range but not in the percentage range (ibid., p. 557).
e) In addition, Kister demonstrates (ibid., p. 563) that the control is not stable to large disturbances. On the contrary, it is even possible that a "runaway" occurs, in which the direction of action of the control circuit is reversed, so that the controller does not reduce but instead increases the deviation and the process moves ever further away from the intended state. The reason for this is that the measured temperature difference has a maximum as a function of the product quality and its gradient reverses after the maximum has been passed. In the case of disturbances which exceed a certain size, the process would therefore become unstable.

There is therefore a need for further improvements in the field of separating a mixture into a plurality of components with the quality of the individual components remaining the same even under altered boundary conditions such as, in particular, pressure fluctuations and changes in the hydraulic loading of the apparatuses used, for instance as a result of changes in the size of the feed stream.

SUMMARY

Taking account of this requirement, the present invention provides:

A method for operating a rectification column (1000) for separating a mixture (S) containing a component A and a component B having a boiling point higher than that of the component A at an operating pressure of the rectification column (1000) below ambient pressure, wherein the sum of the mass fractions of the components A and B in the mixture (S) is, based on its total mass, at least 95.0% and wherein a first product stream (P1) comprising the component A and a second product stream (P2) comprising the component B (and optionally further streams, in particular low boiler-containing streams (A21) and high boiler-containing streams (B11)) are obtained from the mixture (S);

wherein the rectification column (1000) comprises (at least) the following devices:

(I) a vertical column body (100) comprising a stripping section (110) with separating internals and a rectifying section (120) arranged thereover and having separating internals;

(II) a column bottom (130) below the stripping section to accommodate a liquid bottom fraction (B1), wherein a first temperature measuring device (TM1) for measuring a first reference temperature (T1) is arranged in the stripping section (110) or in the column bottom (130);

(III) a column top (140) above the rectifying section to accommodate a gaseous overhead fraction (A1);

(IV) a feeding point (150) for the mixture (S) arranged between the stripping section (110) and the rectifying section (120), wherein the mixture (S) is fed into the rectification column (1000) at a mass flow $\dot{m}_s$;

(V) an evaporator (200) for heating the column bottom (130) (for example by indirect heating of a part (B12) of the bottom fraction (B1) by means of a heat transfer medium (VV) such as, in particular, steam);

(VI) a bottom outlet unit or side outlet unit (220) for discharging the second product stream (P2) at a mass flow $\dot{m}_{P2}$;

(VII) a condenser (300) (arranged within or outside the rectification column (1000)) for partially condensing the gaseous overhead fraction (A1) to give a liquid overhead fraction (A2) and a fraction composed of uncondensed constituents (A3) (comprising low boilers and possibly present gases which are not condensable under normal industrial conditions (minimum condensation temperature −20° C.) (for example inert gases));

(VIII) a top outlet unit or side outlet unit (310) for taking off the first product stream (P1) as a first part of a distillate fraction (A4) at a mass flow $\dot{m}_{P1}$, wherein a second part of the distillate fraction (A4) is conveyed as reflux (A42) at a mass flow $\dot{m}_{A42}$ in such a way that the reflux (A42) travels through at least part of the rectifying section (120) so that a reflux ratio $r=\dot{m}_{A42}/\dot{m}_{P1}$ is established (with the distillate fraction (A4) being able to comprise the liquid overhead fraction (A2) or constituents thereof or being able to be identical to the liquid overhead fraction (A2));

(IX) a second temperature measuring device (TM2) for measuring a second reference temperature (T2) which is arranged in the rectifying section (120) or in the column top (140); and (XI) a third temperature measuring device (TM3) for measuring a control temperature (TC) which is arranged in the column body (100) between the first temperature measuring device (TM1) and the second temperature measuring device (TM2);

wherein the method comprises a step for controlling the mass fraction of the component B in the first product stream (P1) to a value within a first target range from 0.1% to 5.0%, based on the total mass of the first product stream (P1), and the mass fraction of the component A in the second product stream (P2) to a value within a second target range from 0.1% to 5.0%, based on the total mass of the second product stream (P2), wherein the control is carried out as a function of the control temperature (TC) for which a setpoint $TC_{setpoint}$ is calculated according to the equation $$TC_{setpoint}=T2+F\cdot(T1-T2),$$

where F is a factor in the range from 0.1 to 0.9;

wherein the first reference temperature (T1), the second reference temperature (T2) and the control temperature (TC) are measured continuously or at intervals and wherein in the case of a deviation of the measured control temperature (TC) from its setpoint $TC_{setpoint}$ being found the control temperature (TC) is readjusted to the setpoint $TC_{setpoint}$ by varying one or more of the following actuating variables:

(i) the heating of the column bottom (130) by the evaporator (200), (ii) the mass flow $\dot{m}_{A42}$ of the reflux (A42) fed back into the rectification column, (iii) the mass flow $\dot{m}_{P2}$ of the second product stream (P2) and (iv) the mass flow $\dot{m}_{P1}$ of the first product stream (P1).

For the purposes of the present invention, a rectification column is, as those skilled in the art know, a process apparatus for the thermal separation of mixtures which operates according to the principle of rectification, i.e. in which vapor comes into contact a number of times in succession with liquid in counter current. Examples of rectification columns are packed columns or tray columns. The contact area between the vapor phase and liquid phase is provided by separating internals, which make up the stripping section and rectifying section.

The term "separating internals" refers in the terminology of the present invention to installations inside the column body which intensify the contact and mass transfer between vapor phase and liquid phase such that the more volatile constituents tend to be transferred to the vapor phase and the less volatile constituents tend to be transferred to the liquid phase, thereby providing a separation effect in accordance with boiling point differences. Separating internals may be in particular one or more trays or one or more packed beds using structured or random packing.

The term stripping section (110) refers in the terminology of the present invention to the region below the feeding point (150) of the mixture (S) to be separated and encompasses the totality of all separating internals present in this region.

The term rectifying section (120) refers in the terminology of the present invention to the region above the feeding point (150) and comprises the totality of all separating internals in this region. The terminology "separating internals" is customary in the field and does not necessarily imply that stripping section and rectifying section each have to contain a plurality of internals. An embodiment in which stripping section and rectifying section are each formed, for example, by one (1) packed bed (also as depicted in FIG. 1) is encompassed by the present invention. The structure of such separating internals (regardless of whether in the stripping or rectifying section) is known to a person skilled in the art and therefore requires no further explanations at this point. Instead of a rectification column, the term column will also be used for short in the following. The two terms will be used synonymously in the terminology of the present invention.

The components A and B can be pure substances or mixtures, in particular mixtures of isomers. As an example of the latter case, mention may be made of toluenediamine (TDA), without wishing to restrict the invention thereto. TDA occurs in various isomers which, depending on the position of the two amino groups relative to one another, can be referred to as ortho-, meta- and para-TDA. There are in each case various isomers of meta- and ortho-TDA, namely 2,4-TDA, 2,6-TDA and 3,5-TDA for the first and 2,3-TDA and 3,4-TDA for the second. In the industrial production of TDA by hydrogenation of dinitrotoluene (DNT), which is in turn obtained by dinitration of toluene, only the ortho and meta isomers play a role, and in the case of meta-TDA only 2,4-TDA and 2,6-TDA are relevant. 2,5-TDA (para position of the amino groups) and 3,5-TDA (meta position of the amino groups) are, if formed at all, produced only in negligible amounts. During the course of the purification by rectification of the crude TDA obtained from the hydrogenation, ortho- and meta-TDA are separated from one another without the individual isomers being separated since the boiling point differences between the two relevant meta isomers on the one hand and the two ortho isomers on the other hand are very small compared to the boiling point difference between the lowest-boiling meta-TDA isomer and the highest-boiling ortho-TDA isomer. In the terminology of the present invention, ortho-TDA in its totality can then be regarded as component A and meta-TDA in its totality can be regarded as component B, i.e. the component A is in this case a mixture of 2,3- and 3,4-TDA and the component B is a mixture of 2,4- and 2,6-TDA.

The requirement according to the invention that the component B has a higher boiling point than the component A should be interpreted, in the case of one or both components comprising a plurality or constituents, as meaning that the highest-boiling constituent of the component A boils at a lower temperature than the lowest-boiling constituent of the component B.

The term low boilers refers to organic secondary components whose boiling point is below the boiling point of the component A or of the lowest-boiling constituent of the component A. The term high boilers refers to organic secondary components whose boiling point is above the boiling point of the component B or of the highest-boiling constituent of the component B.

The relative volatility α of the two components A and B is a measure of their thermal separability and is expressed as $$\alpha = (y_A \cdot x_B)/(y_B \cdot x_A),$$

where y is the mole fraction of a component in the vapor and x is the mole fraction of a component in the liquid which is in thermodynamic equilibrium with the vapor phase. When A and B in turn consist of a plurality of materials, in particular isomers, y and x are each cumulative parameters. An example is the case in which the component B is meta-TDA, i.e. a mixture of 2,4-TDA and 2,6-TDA (any presence of traces of 3,5-TDA can be disregarded for the purposes of the present invention and does not leave the scope of the invention), and the component A is ortho-TDA, i.e. a mixture of 2,3-TDA and 3,4-TDA. The mole fraction $x_B$ of meta-TDA, $x_{meta-TDA}$, is in this case the sum of the mole fractions of the individual components 2,4-TDA and 2,6-TDA. If the molar amount of 2,4-TDA or 2,6-TDA in the liquid is designated as $n_{2,4-TDA(L)}$ or $n_{2,6-TDA(L)}$, respectively, and the total molar amount in the liquid is designated by $n_{(L)}$, the following equation thus applies:

$$x_B = x_{meta-TDA} = [n_{2,4-TDA(L)}/n_{(L)}] + [n_{2,6-TDA(L)}/n_{(L)}].$$

A corresponding equation applies for $x_A$, $y_A$, and $y_B$.

The mixture (S), the separation of which is the focus of the invention, can contain up to 5.0% by mass of impurities in addition to the components A and B. If no further streams apart from the product streams P1 and P2 are taken off from the rectification column (1000), such impurities then go, depending on their boiling points, together with the component A into the product stream P1 (if they are not very volatile impurities which are discharged by stream A3) or together with the component B into the product stream P2. If necessary, the product streams P1 and P2 can be freed of such impurities in further distillation steps.

All pressures reported are absolute pressures. In the terminology of the present invention, the expression "operating pressure of the rectification column" refers to the pressure at the top of the column.

It has surprisingly been found that the abovementioned problems in the field of separation of a mixture into a plurality of components with the quality of the individual components being unchanged can be solved or at least alleviated when the rectification column used for separating the mixture is operated by the method of the invention.

DETAILED DESCRIPTION

Figure 1:
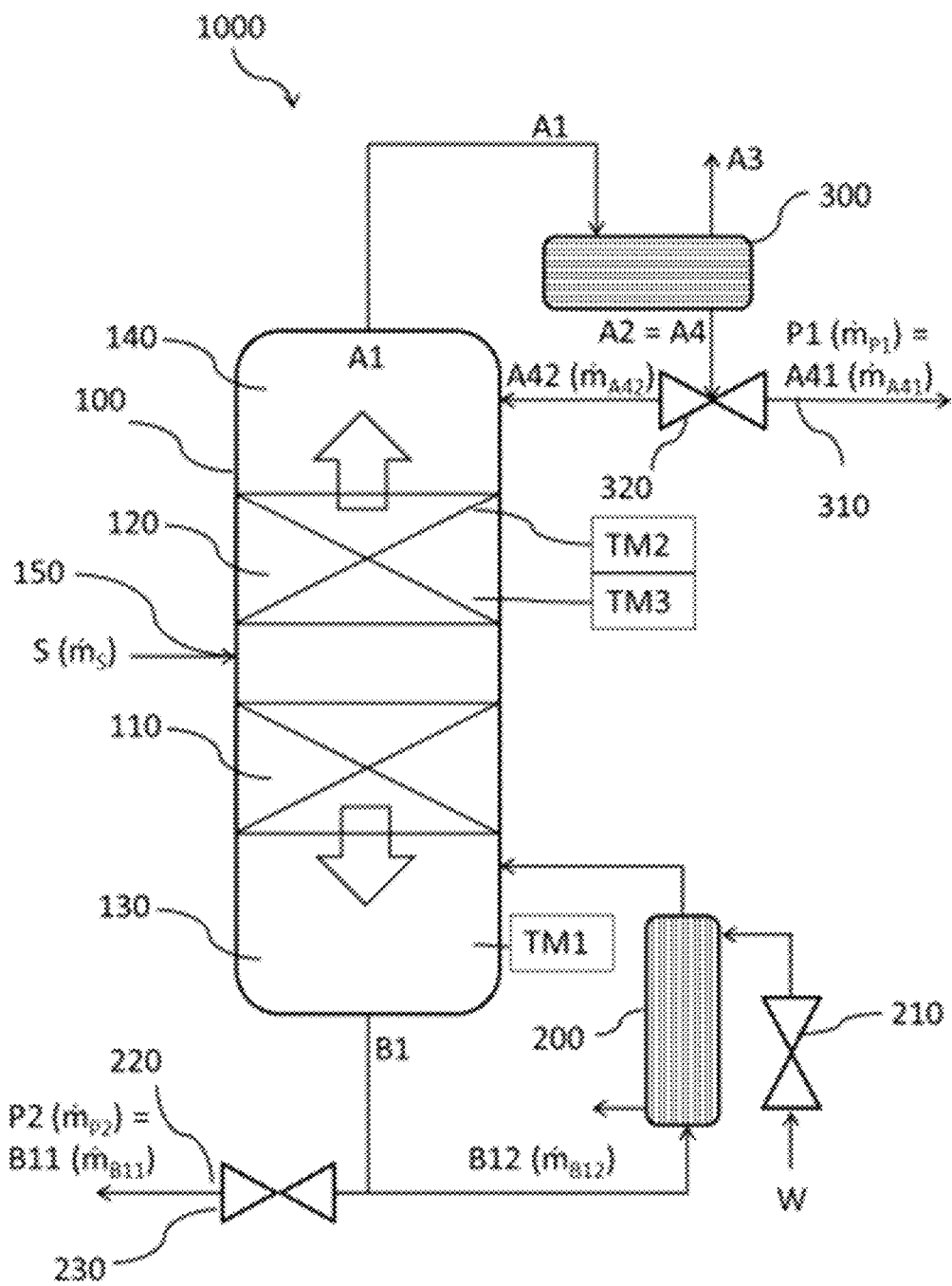
FIG. 1 a possible embodiment of a rectification column (1000) which can be operated according to the method of the invention, with withdrawal of the first product stream (P1) at the top and of the second product stream (P2) from the bottom.

A brief summary of various possible embodiments of the invention firstly follows:

In a first embodiment of the invention, which can be combined with all other embodiments, the component A and the component B have a relative volatility $\alpha$ in the range from 1.05 to 10.

In a second embodiment of the invention, which is a particular configuration of the first embodiment, the relative volatility $\alpha$ is in the range from 1.3 to 3.

In a third embodiment of the invention, which can be combined with all other embodiments, the first temperature measuring device (TM1) is arranged in the column bottom.

In a fourth embodiment of the invention, which can be combined with all other embodiments, the third temperature measuring device (TM3) is arranged at a position within the column body (100) at which the component A is present in a mass fraction, based on the total mass of A and B, in the range from 30% to 70% (and the component B is consequently present in a mass fraction, based on the total mass of A and B, of from 70% to 30%).

In a fifth embodiment of the invention, which can be combined with all other embodiments, the factor F is in the range from 0.3 to 0.7.

In a sixth embodiment of the invention, which can be combined with all other embodiments, the operating pressure (in the column top (140)) is set to a value $p_B$, with the value $p_B$ fluctuating by not more than ±35% during operation of the rectification column (1000).

In a seventh embodiment of the invention, which can be combined with all other embodiments, the following steps are carried out in order to determine the factor F:

(A) determination of a permissible concentration range of the component B in the first product stream (P1) within the first target range (wherein this permissible concentration range may also be identical to the first target range) and a permissible concentration range of the component A in the second product stream (P2) within the second target range (wherein this permissible concentration range may also be identical to the second target range);

(B) establishment of requirements which the rectification column (1000) has to meet, taking into account the permissible concentration range of the component B in the first product stream (P1) and the permissible concentration range of the component A in the second product stream (P2), where the requirements encompass the number of theoretical plates, the location of the feeding point (150) and the operating pressure;

(C) determination of a temperature profile of the rectification column from the requirements established in (B) by a computer-aided simulation and/or measurements (in particular in an experimental plant);

(D) determination of the dependence of the temperature profile on changes in an operating condition and establishment of the position thereof within the temperature profile at which this dependence is at a maximum, where the operating condition is one or more of the following:

the heating of the column bottom (130) by the evaporator (200), the reflux ratio r, the mass flow of the first product stream P1 ($\dot{m}_{P1}$), the mass flow of the second product stream P2 ($\dot{m}_{P2}$), the composition of the feed and the mass flow of the feed ($\dot{m}_s$);

(E) establishment of the positions of the first temperature measuring device (TM1) in the column bottom (130) or in the stripping section (110), of the second temperature measuring device (TM2) in the column top (140) or in the rectifying section (120) and of the third temperature measuring device (TM3) at the position of maximum dependence of the temperature profile on changes in an operating condition as determined in (D) (wherein such deviations from this "ideal" or "theoretical" position of maximum dependence, which are due only to spatial circumstances, for example because the position of maximum dependence as determined in (D) is located in internals and the installation of a temperature measuring device at this position is not possible, do not leave the scope of this embodiment);

(F) determination of the factor F under the boundary conditions established in (A) to (E) by computer-aided simulation and/or measurements (in the rectification column under consideration or an experimental plant);

and in which the following steps are carried out in order to determine the setpoint $TC_{setpooint}$ of the control temperature TC by means of the factor F determined in (F):

(G) input of the factor F into a process control system which controls the rectification column (1000);

(H) calculation of the setpoint $TC_{setpoint}$ of the control temperature (TC) from the first reference temperatures (T1) measured during operation of the rectification column (1000) and the second reference temperature (T2) measured during operation of the rectification column (1000).

In an eighth embodiment of the invention, which can be combined with all other embodiments, the component A comprises a mixture of 2,3-toluenediamine and 3,4-toluenediamine and the component B comprises a mixture of 2,4-toluenediamine and 2,6-toluenediamine.

In a ninth embodiment of the invention, which is a particular configuration of the eighth embodiment, the column bottom (130) is heated by the evaporator (200) to a temperature in the range from 150° C. to 250° C.

In a tenth embodiment of the invention, which is a particular configuration of the eighth and ninth embodiments, the reflux ratio r is in the range from 20 to 100.

In an eleventh embodiment of the invention, which is a particular configuration of the eighth to tenth embodiment, a value $p_B$ in the range from 50 mbar to 250 mbar is set for the operating pressure (measured in the column top (140)).

In a twelfth embodiment of the invention, the rectification column (1000) is a packed column. This embodiment can be combined with all other embodiments as long as they do not exclude the rectification column (1000) being configured as a packed column.

In a thirteenth embodiment of the invention, the rectification column (1000) is a tray column. This embodiment can be combined with all other embodiments as long as these do not exclude the rectification column (1000) being configured as a tray column.

The embodiments indicated above and further possible variants of the invention will be explained in more detail below. All embodiments and further implementation options can be combined with one another in any way, unless the contrary is unambiguously indicated by the context to a person skilled in the art or something different is expressly said.

Since temperature measurements have a significantly greater accuracy than pressure measurements, only these are used in order to perform the control task in the method of the invention. Furthermore, the measured boiling point is a function of the pressure for a fixed composition and in particular for a pure material. The temperatures at the top (or in the rectifying section) and in the bottom (or in the stripping section) of the column can thus be used as indicators for the pressures there.

In the following, a column which is in the intended state with respect to the product quality to be controlled but is operated at various pressures will be discussed. An increase in the pressure at the top leads to a corresponding increase in pressure over the entire column. This gives a comparable temperature increase both in the bottom and in the top and at the position where the control temperature is measured. Thus, the ratio $$(TC-T2)/(T1-T2)$$

remains approximately constant.

If the differential pressure over the column then increases, the pressure and thus also the temperature at the top (or in the rectifying section) remain constant, while pressure and temperature at the point where the control temperature is measured and in the bottom (or in the stripping section) increase. Here, the increase in pressure and temperature is greatest in the bottom since the differential pressure over the entire column is decisive for this, while only the differential pressure between the measurement position and the top is decisive for pressure and temperature at the position at which the control temperature is measured.

The invention is based, inter alia, on the finding that, particularly when the components A and B have a relative volatility α in the range from 1.05 to 10, particularly preferably in the range from 1.3 to 3, the ratio $$(TC-T2)/(T1-T2)$$

remains approximately constant even when the pressure changes, as long as the pressure change is not too great (in particular not more than 35%, preferably not more than 30%, of the original pressure, i.e. the pressure before occurrence of the pressure change).

It follows from this that, when the column is operated correctly with respect to the product quality to be controlled, the ratio $(TC-T2)/(T1-T2)$ remains approximately constant even when the overhead pressure or differential pressure in the column change.

This fact is utilized by the newly developed control concept: the ratio $(TC-T2)/(T1-T2)$ is calculated on the basis of the temperatures in the intended state of the column and stored as constant factor F. A temperature $TC_{CALC}$, which would be obtained at the measurement position in the intended state, can then be calculated during operation of the column with the aid of the equation $$TC_{CALC}=T2+F\cdot(T1-T2),$$

of the factor F and the measured temperatures T1 and T2. The calculated temperature is then used as setpoint $TC_{setpoint}$ for the control temperature, i.e. $TC_{setpoint}=TC_{CALC}$.

A P (proportional) controller, PI (proportional-integral) controller, PID (proportional-integral-differential) controller or another comparable building block for control, preferably a PI controller, is normally used for control. The controller output preferably influences the evaporator duty supplied (i), the reflux flow directly or indirectly (ii) or one of the product streams P2 (iii) or P1 (iv) directly or indirectly. In the case of direct influencing, the controller output can directly control the setting of the valve, while in the case of indirect influencing the regular output would serve as setpoint for, for example, a flowrate controller, the controller output of which then controls the setting of the valve.

A rectification column (1000) which can be operated using the method of the invention is shown by way of example in FIG. 1. (The accompanying drawings show rectification columns suitable for use of the method of the invention for the example of packed columns. Other types of rectification columns such as tray columns are of course likewise suitable.)

The mixture (S) to be separated is fed to the rectification column (1000) at a mass flow $\dot{m}_s$ in the middle region of the column (1000) via a feeding point (150). Stripping section (110) and rectifying section (120) each consist of a packed bed in the chosen example. This should be interpreted as merely illustrative and not constituting any restriction.

The column bottom (130) is heated indirectly by means of a heat transfer medium (W), in particular steam, using an evaporator (200), which is configured as heat exchanger, by recirculating a part (B12 with the mass flow $\dot{m}_{B12}$) of the bottom fraction (B1) taken off at the lower end of the column (1000) into the column (1000) via the evaporator (200). The amount of the heat transfer medium (W) introduced and thus the heating duty can be set via a heat transfer medium valve (210). The second product stream (P2) is in this embodiment a further part (=B11) of the bottom fraction (B1) and is taken off from the column (1000) at a mass flow $\dot{m}_{P2}$ (in this embodiment identical to $\dot{m}_{B11}$). The ratio of the mass flows $\dot{m}_{B12}$ and $\dot{m}_{B11}$ is set by means of a bottoms circuit valve (230).

At the column top (140), a vaporized overhead fraction (A1) is taken off and partially liquified in a condenser (300) arranged outside the column body (100). The arrangement of the condenser (300) outside the column body (100) is not absolutely necessary (see also FIG. 2 and FIG. 3). Uncondensed constituents (A3) are taken off in gaseous form. These uncondensed constituents (A3) comprise impurities having a boiling point below that of the second product stream (P2) (known as low boilers) and any present gases which are not condensable under customary industrial conditions (minimum condensation temperature −20° C.) (for example inert gases). The condensed constituents (A2), which in this embodiment are identical to the distillate fraction (A4), are divided by means of a reflux splitter (320) into a stream A42 which is recirculated at the mass flow $\dot{m}_{A42}$ to the column (1000) and into a stream A41 which is the first product stream (i.e. P1=A41) and which is taken off at a mass flow $\dot{m}_{P1}$ (=$\dot{m}_{441}$). In the embodiment of FIG. 1, the first product stream (P1) thus has a composition identical to that of the liquid overhead fraction (A2). The ratio of the mass flows $\dot{m}_{442}/\dot{m}_{P1}$ is referred to as reflux ratio (r).

Figure 2:
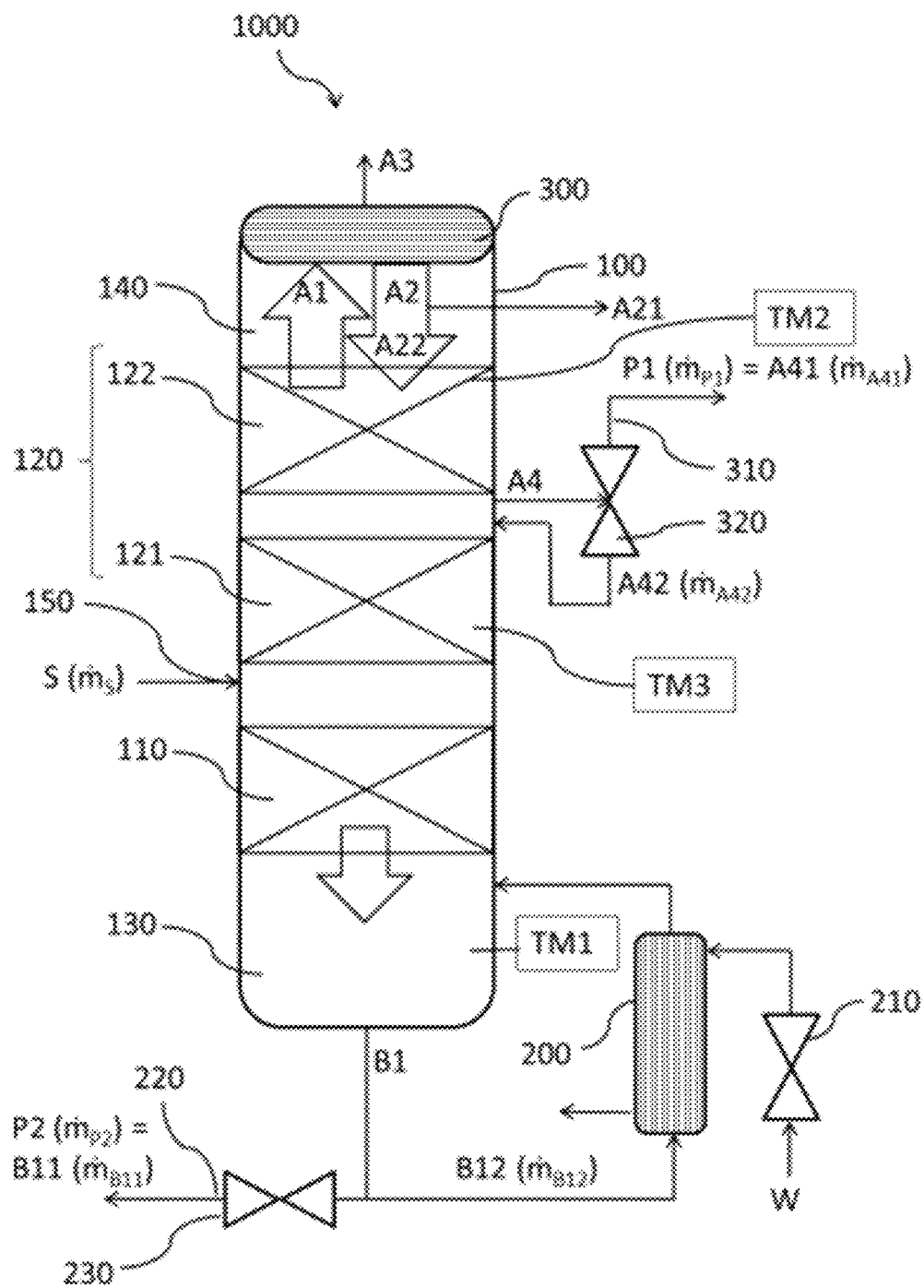
FIG. 2 a possible embodiment of a rectification column (1000) which can be operated according to the method of the invention, with withdrawal of the first product stream (P1) as side stream and of the second product stream (P2) as bottom stream. In the embodiment shown, the rectifying section (120) is made up of two packed beds (121) and (122).

FIG. 2 shows a further possible configuration of a rectification column (1000) which can be operated using the method of the invention. Reference numerals which are repetitions have the same meaning as in FIG. 1. In contrast to the column shown in FIG. 1, the condenser (300) here is located in the top of the column and the rectifying section (120) is formed by two packed beds (121, 122) which are located above and below a side outlet for the distillate fraction (A4). The second temperature measuring device (TM2) can be arranged in each of the two packings (121, 122). The condensate obtained in the condenser (300) (=the liquid overhead fraction (A2)) flows in the interior of the column body (100) downwards through the upper part (122) of the rectifying section (120) in this embodiment. Below the packed bed (122), there is a liquid collector (not shown) in which liquid (A22) trickling down from the upper packed bed (122) is collected and discharged from the column body (100) as distillate fraction (A4). The distillate fraction (A4) is, as described for FIG. 1, divided into the reflux (A42) and the first product stream (P1=A41). As an alternative, only the first product stream (P1) can also be discharged from the column body (100), while the reflux stream is fed within the column body to the lower packed bed (121). As shown in FIG. 2, it is possible to discharge a low boiler-containing stream (A21) from the liquid overhead fraction (A2). Depending on how much of the component A is still present in this low boiler stream and the magnitude of this, it can be useful to feed the stream A21 to a further distillation in order to isolate A. However, the mass ratio of the streams A21 to A22 is in such a case typically quite small and is in particular in the range from 0.001 to 0.05. Whether withdrawing lower boilers (A21) in this manner is useful depends on the specific separation task, in particular on the low boiler content of the mixture S, and can easily be decided by a person skilled in the art in the particular case.

Figure 3:
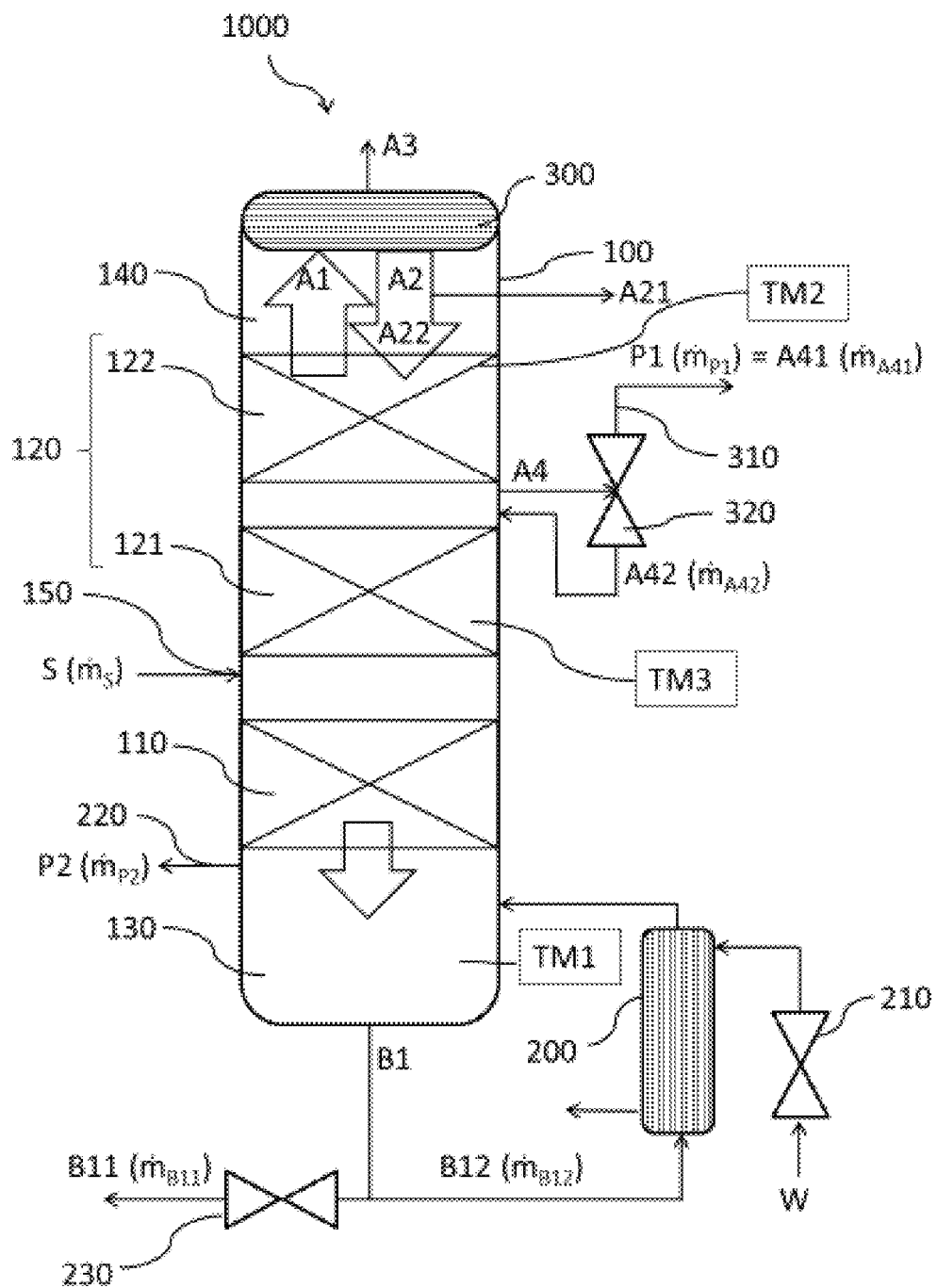
FIG. 3 a further possible embodiment of a rectification column (1000) which can be operated according to the method of the invention, with withdrawal of the first product stream (P1) and of the second product stream (P2) as side streams.

FIG. 3 shows a variation of the embodiment shown in FIG. 2, in which the second product stream (P2) is obtained as side stream directly below the stripping section (110) while the discharged part (B11) of the bottom stream (B1) is used for taking off high boilers. In this embodiment, the second product stream (P2) is thus different from the stream B11. Depending on how much of the component B is present in the stream B11 and the magnitude of this, it can be useful to feed stream B11 to a further distillation to isolate B. The configuration as shown in FIG. 3 can be useful particularly when the mixture S to be separated contains a comparatively large amount of high boilers. If a large amount of high boilers but only a small amount of low boilers are present, the low boiler outlet A21 can also be dispensed with, as already indicated above.

The implementation options of the rectification column (1000) shown in the figures should not be interpreted as being exhaustive. It is, for example, possible and within the scope of the present invention for the gaseous fraction composed of uncondensed constituents (A3) to be subjected to an after-condensation in order to obtain a liquid stream containing secondary components having a boiling point lower than that of the component A (known as low boilers).

Regardless of the precise configuration of the rectification column, the following embodiments are preferred:

Preference is given to the first temperature measuring device (TM1) being arranged in the column bottom.

As regards the positioning of the third temperature measuring device (TM3), this is preferably arranged at a position within the column body (100) at which the component A is present in a mass fraction, based on the total mass of A and B, in the range from 30% to 70% (and the component B is consequently present in a mass fraction, based on the total mass of A and B, of from 70% to 30%).

According to the invention, the factor F is in the range from 0.1 to 0.9, preferably in the range from 0.3 to 0.7. To determine a specific value for the factor F, the following procedure is preferably employed:

(A) determination of a permissible concentration range of the component B in the first product stream (P1) within the first target range (wherein this permissible concentration range can also be identical to the first target range) and a permissible concentration range of the component A in the second product stream (P2) within the second target range (wherein this permissible concentration range can also be identical to the second target range);

(B) establishment of requirements which the rectification column (1000) has to meet, taking into account the permissible concentration range of the component B in the first product stream (P1) and the permissible concentration range of the component A in the second product stream (P2), where the requirements encompass the number of theoretical plates, the location of the feeding point (150) and the operating pressure;

(C) determination of a temperature profile of the rectification column from the requirements established in (B) by a computer-aided simulation and/or measurements (in particular in an experimental plant);

(D) determination of the dependence of the temperature profile on changes in an operating condition and establishment of the position thereof within the temperature profile at which this dependence is at a maximum, where the operating condition is one or more of the following:
the heating of the column bottom (130) by the evaporator (200), the reflux ratio r, the mass flow of the product stream P1 ($\dot{m}_{P1}$), the mass flow of the product stream P2 ($\dot{m}_{P2}$), the composition of the feed and the mass flow of the feed ($\dot{m}_s$);

(E) establishment of the positions of the first temperature measuring device (TM1) in the column bottom (130) or in the stripping section (110), of the second temperature measuring device (TM2) in the column top (140) or in the rectifying section (120) and of the third temperature measuring device (TM3) at the position of maximum dependence of the temperature profile on changes in an operating condition as determined in (D) (wherein such deviations in this "ideal" or "theoretical" position of maximum dependence, which are due only to spatial circumstances, for example because the position of maximum dependence as determined in (D) is located in internals and the installation of a temperature measuring device at this position is not possible, do not leave the scope of this embodiment);

(F) determination of the factor F under the boundary conditions established in (A) to (E) by computer-aided simulation and/or measurements (in the rectification column under consideration or an experimental plant);

and in which the following steps are carried out in order to determine the setpoint $TC_{setpoint}$ of the control temperature TC by means of the factor F determined in (F):

(G) input of the factor F into a process control system which controls the rectification column (1000);

(H) calculation of the setpoint $TC_{setpoint}$ of the control temperature (TC) from the temperatures T1 and T2 measured during operation of the rectification column (1000).

The method of the invention can be used, for example, in the work-up of toluenediamine (TDA), in particular in a step for separating meta and ortho isomers from one another. In this case, the component A comprises a mixture of 2,3-TDA and 3,4-TDA and the component B comprises a mixture of 2,4-TDA and 2,6-TDA. Preferred operating parameters for this use are as follows:

The temperature in the column bottom (130) is set by means of the evaporator (200) to a temperature in the range from 150° C. to 250° C.

The reflux ratio r is set to a value in the range from 20 to 100.

The operating pressure ($p_B$) is set to a value in the range from 50 mbar to 250 mbar.

In this way, the column denoted "A" in U.S. Pat. No. 6,359,177, for example, can be operated according to the method of the invention. It is also conceivable to operate the dividing wall column described in EP 1 746 083 A1 according to the method of the invention.

The invention will be illustrated in detail below with the aid of examples.

EXAMPLES

General Conditions (Base Case)

The separation of an isomer mixture of a feed S consisting of 8000 kg/h of 2,4-TDA, 2000 kg/h of 2,6-TDA, 200 kg/h of 2,3-TDA and 300 kg/h of 3,4-TDA was simulated with the aid of a process simulation program (VTPLAN, comparable to ASPEN). Here, a column having 20 theoretical plates was assumed and the feed S was introduced at theoretical plate 13. An evaporator was located at the bottom of the column, and a condenser was present at the top. An overhead pressure of 100 mbar and a bottom pressure of 120 mbar were assumed. The condensation temperature was set to 150° C. Evaporator duty and reflux were varied so that the concentration of 2,3- and 3,4-TDA (ortho-TDA) in the product stream P2 and the concentration of 2,4- and 2,6-TDA (meta-TDA) in the product stream P1 was in each case 1.0%. An evaporator duty of 1653 kW and a reflux flow $\dot{m}_{A42}$ of 9468 kg/h were established. In the simulation calculation, it was found that at theoretical plate 7 the concentrations of meta-TDA and ortho-TDA are approximately equal and the gradient of the temperature profile is particularly steep. A temperature of 195° C. was found at theoretical plate 7, and this theoretical plate will be used for controlling the temperature in the following. A temperature for T2 of 185° C. was found at the top and a temperature for T1 of 211° C. was found in the bottom.

Example 1 (Comparison)

In a simulation as described in the general conditions, the evaporator duty was fixed at a constant 1653 kW. The control temperature was fixed at 195° C. In order to simulate a disturbance in the pressure, the pressure in the column was increased by 30 mbar uniformly over the entire column. In the simulation, this resulted in an increase in the content of ortho-TDA in the stream P2 to 3.0%, while the stream P1 now contained only 0.12% of meta-TDA.

Example 2 (According to the Invention)

In a simulation as described in the general conditions, the evaporator duty was fixed as in the example which is not according to the invention and the pressure was increased by 30 mbar. The factor F is calculated as 0.42 from the simulation calculation of the base case. As a result of the pressure change, the calculated temperature T1 increased to 218° C. and T2 increased to 192° C. A control temperature of 203° C. was calculated using the factor F.

In the simulation, this was set at theoretical plate 7. A content of ortho-TDA in the stream P2 of 1.1% and of meta-TDA in the stream P1 of 1.1% were found.

The invention claimed is:

1. A method for operating a rectification column (1000) for separating a mixture (S) containing a component A and a component B having a boiling point higher than that of the component A at an operating pressure of the rectification column (1000) below ambient pressure, wherein a sum of mass fractions of the components A and B in the mixture (S) is, based on a total mass of the mixture (S), 95.0% to 100%, and wherein a first product stream (P1) comprising the component A and a second product stream (P2) comprising the component B are obtained from the mixture (S);

wherein the rectification column (1000) comprises:
(I) a vertical column body (100) comprising a stripping section (110) with separating internals and a rectifying section (120) arranged over top of the stripping section (110) and having separating internals;
(II) a column bottom (130) arranged below the stripping section (110) to accommodate a liquid bottom fraction (B1), wherein a first temperature measuring device (TM1) for measuring a first reference temperature (T1) is arranged in the stripping section (110) or in the column bottom (130);
(III) a column top (140) arranged above the rectifying section to accommodate a gaseous overhead fraction (A1);
(IV) a feeding point (150) for the mixture (S) arranged between the stripping section (110) and the rectifying section (120), wherein the mixture (S) is fed into the rectification column (1000) at a mass flow $\dot{m}_s$;
(V) an evaporator (200) for heating the column bottom (130);
(VI) a bottom outlet unit or side outlet unit (220) for discharging the second product stream (P2) at a mass flow $\dot{m}_{P2}$;
(VII) a condenser (300) arranged within or outside the rectification column (1000) for partially condensing the gaseous overhead fraction (A1) to give a liquid overhead fraction (A2) and a fraction composed of uncondensed constituents (A3);
(VIII) a top outlet unit or side outlet unit (310) for taking off the first product stream (P1) as a first part of a distillate fraction (A4) at a mass flow $\dot{m}_{P1}$, wherein a second part of the distillate fraction (A4) is conveyed as reflux (A42) at a mass flow $\dot{m}_{A42}$ in such a way that the reflux (A42) travels through at least part of the rectifying section (120) so that a reflux ratio $r=\dot{m}_{A42}/\dot{m}_{P1}$ is established;
(IX) a second temperature measuring device (TM2) for measuring a second reference temperature (T2), wherein the second temperature measuring device is arranged in the rectifying section (120) or in the column top (140); and
(XI) a third temperature measuring device (TM3) for measuring a control temperature (TC), wherein the third temperature measuring device (TM3) is arranged in the column body (100) between the first temperature measuring device (TM1) and the second temperature measuring device (TM2);

wherein the method comprises operating the rectification column (1000) at a pressure below ambient pressure and controlling a mass fraction of the component B in the first product stream (P1) to a value within a first target range from 0.1% to 5.0%, based on a total mass of the first product stream (P1), and a mass fraction of the component A in the second product stream (P2) to a value within a second target range from 0.1% to 5.0%, based on a total mass of the second product stream (P2), wherein the controlling is carried out as a function of the control temperature (TC) for which a setpoint $TC_{setpoint}$ is calculated according to an equation $$TC_{setpoint} = T2 + F \cdot (T1 - T2),$$

where F is a factor in the range from 0.1 to 0.9;

wherein the first reference temperature (T1), the second reference temperature (T2) and the control temperature (TC) are measured continuously or at intervals and when there is a deviation of a measured control temperature (TC) from the set point $TC_{setpoint}$ the control temperature (TC) is adjusted to the setpoint $TC_{setpoint}$ by adjusting one or more of the following actuating variables:

(i) the heating of the column bottom (130) by the evaporator (200), (ii) the mass flow $\dot{m}_{A42}$ of the reflux (A42) fed back into the rectification column, (iii) the mass flow $\dot{m}_{P2}$ of the second product stream (P2) and (iv) the mass flow $\dot{m}_{P1}$ of the first product stream (P1).

2. The method according to claim 1, wherein the component A and the component B have a relative volatility α in the range from 1.05 to 10.

3. The method according to claim 2, wherein the relative volatility α is in the range from 1.3 to 3.

4. The method according to claim 1, wherein the first temperature measuring device (TM1) is arranged in the column bottom.

5. The method according to claim 1, wherein the third temperature measuring device (TM3) is arranged at a position within the column body (100) at which the component A is present in a mass fraction, based on the total mass of A and B, in the range from 30% to 70%.

6. The method according to claim 1, wherein the factor F is in the range from 0.3 to 0.7.

7. The method according to claim 1, wherein the operating pressure is set to a value $p_B$, wherein the value $p_B$ does not fluctuate by more than ±35% during operation of the rectification column (1000).

8. The method according to claim 1, wherein determining the factor F comprises:

(A) determining a permissible concentration range of the component B in the first product stream (P1) within the first target range and a permissible concentration range of the component A in the second product stream (P2) within the second target range;

(B) establishing requirements which the rectification column (1000) has to meet, taking into account the permissible concentration range of the component B in the first product stream (P1) and the permissible concentration range of the component A in the second product stream (P2), where the requirements encompass the number of theoretical plates, the location of the feeding point (150) and the operating pressure;

(C) determining a temperature profile of the rectification column from the requirements established in (II) by a computer-aided simulation and/or measurements;

(D) determining the dependence of the temperature profile on changes in an operating condition and establishment of the position thereof within the temperature profile at which this dependence is at a maximum, where the operating condition is one or more of: the heating of the column bottom (130) by the evaporator (200), the reflux ratio r, the mass flow of the first product stream P1 ($\dot{m}_{P1}$), the mass flow of the second product stream P2 ($\dot{m}_{P2}$), the composition of the feed, and the mass flow of the feed ($\dot{m}_s$);

(E) establishing the positions of the first temperature measuring device (TM1) in the column bottom (130) or in the stripping section (110), of the second temperature measuring device (TM2) in the column top (140) or in the rectifying section (120), and of the third temperature measuring device (TM3) at the position of maximum dependence of the temperature profile on changes in an operating condition as determined in (IV);

(F) determining the factor F under the boundary conditions established in (A) to (E) by computer-aided simulation and/or measurements;

and in which the following steps are carried out in order to determine the setpoint $TC_{setpoint}$ of the controlling temperature TC by means of the factor F determined in (F):

(G) inputting the factor F into a process control system which controls the rectification column (1000); and (H) calculating the setpoint $TC_{setpoint}$ of the control temperature (TC) from the first reference temperatures (T1) measured during operation of the rectification column (1000) and the second reference temperature (T2) measured during operation of the rectification column (1000).

9. The method according to claim 1, wherein the component A comprises a mixture of 2,3-toluenediamine and 3,4-toluenediamine and the component B comprises a mixture of 2,4-toluenediamine and 2,6-toluenediamine.

10. The method according to claim 9, wherein the column bottom (130) is heated by the evaporator (200) to a temperature in the range from 150° C. to 250° C.

11. The method according to claim 9, wherein the reflux ratio r is in the range from 20 to 100.

12. The method according to claim 9, wherein a value pB in the range from 50 mbar to 250 mbar is set for the operating pressure measured in the column top (140).

13. The method according to claim 1, wherein the rectification column (1000) is a packed column.

14. The method according to claim 1, wherein the rectification column (1000) is a tray column.

15. The method according to claim 1, wherein the factor F is calculated according to the equation, $$F = (TC_{INT} - T2_{INT})/(T1_{INT} - T2_{INT}),$$

where $T1_{INT}$ is the first reference temperature in an intended state of the rectification column, $T2_{INT}$ is the second reference temperature in the intended state of the rectification column, and $TC_{INT}$ is the control temperature in the intended stated of the rectification column.

* * * * *